US010538553B2

(12) United States Patent
Cai et al.

(10) Patent No.: US 10,538,553 B2
(45) Date of Patent: Jan. 21, 2020

(54) COMPOUNDS FOR THE TREATMENT OF NEURODEGENERATIVE DISEASES

(71) Applicants: Jianfeng Cai, Tampa, FL (US); Chuanhai Cao, Tampa, FL (US)

(72) Inventors: Jianfeng Cai, Tampa, FL (US); Chuanhai Cao, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/240,673

(22) Filed: Jan. 4, 2019

(65) Prior Publication Data
US 2019/0211059 A1 Jul. 11, 2019

Related U.S. Application Data

(60) Provisional application No. 62/614,204, filed on Jan. 5, 2018.

(51) Int. Cl.
*C07K 7/02* (2006.01)
*A61P 25/28* (2006.01)
*A61K 38/00* (2006.01)

(52) U.S. Cl.
CPC .............. *C07K 7/02* (2013.01); *A61P 25/28* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,880,635 A | 11/1989 | Janoff et al. | |
| 4,906,477 A | 3/1990 | Kurono et al. | |
| 4,911,928 A | 3/1990 | Wallach | |
| 4,917,951 A | 4/1990 | Wallach | |
| 4,920,016 A | 4/1990 | Allen et al. | |
| 4,921,757 A | 5/1990 | Wheatley et al. | |
| 5,580,859 A | 12/1996 | Felgner et al. | |
| 5,679,647 A | 10/1997 | Carson et al. | |
| 5,703,055 A | 12/1997 | Felgner et al. | |
| 2005/0031651 A1 | 2/2005 | Gervais | |
| 2013/0266590 A1 | 10/2013 | Straub | |
| 2016/0209422 A1* | 7/2016 | Cai | A61K 51/0406 |
| 2017/0058002 A1 | 3/2017 | Cai | |
| 2017/0232055 A1 | 8/2017 | Cai | |

OTHER PUBLICATIONS

Bai "Cell Permeability Studies of AApeptides and Novel Molecular Probes for AD" Graduate Theses and Dissertations scholarcommons. usf.edu/etd/6173 (Year: 2016).*
Crews "Role of Synucleins in Alzheimer's Disease" Neurotox Res (2009) 16:306-317 (Year: 2009).*
USF "Novel Molecule for the Treatment of Neurodegenerative Diseases" accesed from usf.edu on Apr. 25, 2019 (Year: 2019).*
C.T.F.A. Cosmetic Ingredient Handbook, 1992, pp. 587-592.
Donnelly et al., "DNA vaccines," Ann. Rev. Immunol., 1997, 15:617-648.
Gomez-Martinez et al., "N α-Alloc temporary protection in solid-phase peptide synthesis. The use of amine-borane complexes as allyl group scavengers," J. Chem. Soc., Perk. T 1, 1999, 2871-2874.
Heagerty et al., "Time-dependent ROC curves for censored survival data and a diagnostic marker," Biometrics, 2000, 56(2):337-344.
IUPAC 1974 Recommendations for Section E, Fundamental Stereochemistry, in Pure Appl. Chem., 1976, 45, 13-30.
Kyte et al., "A Simple Method for Displaying the Hydropathic Character of a Protein," J. Mol. Biol. 1982, 157, 105-132.
McCutcheon's vol. 1, Emulsifiers & Detergents, 1994, North American Edition, pp. 236-239.
Niu et al., "Identification of gamma-AApeptides with potent and broad-spectrum antimicrobial activity," Chemical communications, 2011, 47, 12197-12199.
Niu et al., "γ-AApeptides bind to RNA by mimicking RNA-binding proteins," Org. Biomol. Chem., 2011, 9, 6604-6609.
Niu et al., "γ-AApeptides: design, synthesis and evaluation ," New Journal of Chemistry, 2011, 35, 542-545.
Remington's Pharmaceutical Sciences, 15th Ed. 1975, pp. 335-337.
Wu et al., "Design and synthesis of unprecedented cyclic γ-AApeptides for antimicrobial development," Chem. Sci., 2012, 3 2570-2575.
Wu et al., "γ-AApeptide-based small-molecule ligands that inhibit Aβ aggregation," Chem. Commun., 2014, 50(40): 5206-5208.
Wu et al., "γ-AApeptide-based small-molecule ligands that inhibit Aβ aggregation," Chem. Commun., 2014, Supporting Documentation, 10 pages.
Agadjanyan et al., "Prototype Alzheimer's disease vaccine using the immunodominant B cell epitope from beta-amyloid and promiscuous T cell epitope pan HLA DR-binding peptide," J. Immunol., 174: 1580-1586, 2005.
Alzheimer's Association, "2012 Alzheimer's disease facts and figures," Alzheimer's & Dement., 8: 131-168, 2012.
Arendash & Cao, "Caffeine and coffee as therapeutics against Alzheimer's disease," J. Alzheimers Dis., 20 (Suppl 1):S117-S126, 2010.
Ashton et al., "Expression of the cannabinoid CB2 receptor in the rat cerebellum: An immunohistochemical study," Neurosci. Lett., 396: 113-116, 2006.
Asuni et al., "GSK3alpha exhibits beta-catenin and tau directed kinase activities that are modulated by Wnt," In. Eur. J. Neurosci., 2006, 24: 3387-3392, 2006.
Athanasiou et al., "Cannabinoid receptor agonists are mitochondrial inhibitors: A unified hypothesis of how cannabinoids modulate mitochondrial function and induce cell death," Biochem. Biophys. Res. Commun., 364(1): 131-7, 2007.
Avila, "Tau aggregation into fibrillar polymers: taupathies," FEBS Lett., 476: 82-92, 2000.
Benford and Caplan, "Psychiatric Sequelae of Spice, K2, and Synthetic Cannabinoid Receptor Agnoists," Psychosomatics, 52(3): 295, 2011.
Benito et al., "Cannabinoid CB2 receptors and fatty acid amide hydrolase are selectively overexpressed in neuritic plaque-associated glia in Alzheimer's disease brains," J. Neurosci., 23: 11136-11141, 2003.
Bisogno & Di Marzo, "Cannabinoid receptors and endocannabinoids: Role in neuroinflammatory and neurodegenerative disorders," CNS Neurol. Disord. Trug Targets, 9: 564-573, 2010.

(Continued)

*Primary Examiner* — Adam Weidner
(74) *Attorney, Agent, or Firm* — Fish & Richardson P.C.

(57) ABSTRACT

Disclosed herein are compounds for the treatment of neurodegenerative diseases and compositions comprising the same.

9 Claims, 6 Drawing Sheets

(56) References Cited

OTHER PUBLICATIONS

Brookmeyer et al., "Forecasting the global burden of Alzheimer's disease," Alzheimers Dement., 3: 186-191, 2007.
Campbell & Gowran, "Alzheimer's disease; taking the edge off with cannabinoids?," Br. J. Pharmacol., 152: 655-662, 2007.
Cao et al., "Caffeine suppresses amyloid-beta levels in plasma and brain of Alzheimer's disease transgenic mice," J. Alzheimers Dis., 17: 681-697, 2009.
Cao et al., "High blood caffeine levels in MCI linked to lack of progression to dementia," J. Alzheimer's Dis., 30: 559-572, 2012.
Chiti & Dobson., "Protein misfolding, functional amyloid, and human disease," Annu. Rev. Biochem., 75: 333-366, 2006.
Cho & Johnson, "Glycogen synthase kinase 3beta phosphorylates tau at both primed and unprimed sites. Differential impact on microtubule binding," J. Biol. Chem., 278: 187-193, 2003.
Costa & Colleoni, "Changes in rat brain energetic metabolism after exposure to anandamide or delta-9-tetrahydrocannabinol," European Journal of Pharmacology, 395(21): 1-7, 2000.
DaRocha-Souto et al., "Activation of glycogen synthase kinase-3 beta mediates beta-amyloid induced neuritic damage in Alzheimer's disease," Neurobiol. Dis., 45: 425-437, 2012.
DeMuro et al., "The Absolute Bioavailability of Oral Melatonin," J. Clin. Pharamcol., 40(7): 781-784, 2000.
Deng et al., "Effects of melatonin on wortmannin-induced tau hyperphosphorylation," Acta Pharmacol. Sin., 26: 519-26, 2005.
Dragicevic et al., "Melatonin treatment restores mitochondrial function in Alzheimer's mice: A mitochondrial protective role of melatonin membrane receptor signaling," J. Pineal Res., 51: 75-86, 2011.
Engel et al., "Chronic lithium administration to FTDP-17 tau and GSK-3beta overexpressing mice prevents tau hyperphosphorylation and neurofibrillary tangle formation, but pre-formed neurofibrillary tangles do not revert," J. Neurochem., 99: 1445-1455, 2006.
Esposito et al., "The marijuana component cannabidiol inhibits beta-amyloid-induced tau protein hyperphosphorylation through Wnt/beta-catenin pathway rescue in PC12 cells," J. Mol. Med. (Berl.), 84(3): 253-258, 2006.
Eubanks et al., "A molecular link between the active componenet of marijuana and Alzheimer's disease pathology," Mol. Pharm., 36: 773-777, 2006.
FDA Drug Label of Marinol ®, URL<https://www.accessdata.fda.gov/drugsatfda_docs/label/2005/018651s021lb1.pdf>, 2004.
Feng, "Melatonin alleviates behavioral deficits associated with apoptosis and cholinergic system dysfunction in the APP 695 transgenic mouse model of Alzheimer's disease," J. Pineal Res., 37(2): 129-136, 2004.
Fishbein et al., "Long-term behavioral and biochemical effects of an ultra-low dose of delta-9-tetrahydrocannabinol (THC): neuroprotection and ERK signaling,"Exp. Brain. Res., 221(4): 437-448, 2012.
Garcia-Mesa, "Melatonin plus physical exercise are highly neuroprotective in the 3xTg-AD mouse," Neurobiol. Aging, 33(6): 1124.e13-1124e29, 2012.
Götz et al., "Modes of Aβ toxicity in Alzheimer's disease," Cell. Mol. Life Sci., 68: 3359-3375, 2011.
Hanger et al., Glycogen synthase kinase-3 induces Alzheimer's disease-like phosphorylation of tau: Generation of paired helical filament epitopes and neuronal localization of the kinase, Neurosci. Lett., 147: 58-62, 1992.
Hernandez et al., "GSK3 and tau: Two convergence points in Alzheimer's disease," J. Alzheimers Dis., 33(Suppl 1): S141-S144, 2013.
Hooper et al., "The GSK3 hypothesis of Alzheimer's disease," J. Neurochem., 104: 1433-1439, 2008.
Hoppe et al., "Amyloid-beta neurotoxicity in organotypic culture is attenuated by melatonin: involvement of GSK-3beta, tau and neuroinflammation," J. Pineal Res., 48(3): 230-238, 2010.
International Search Report and Written Opinion in International Appln. No. PCT/US2019/012428, dated Apr. 22, 2019, 12 pages.

Ionov et al., "Mechanism of neuroprotection of melatonin against beta-amyloid neurotoxicity," Neuroscience, 180: 229-237, 2011.
Ishiguro et al., "Phosphorylation sites on tau by tau protein kinase I, a bovine derived kinase generating an epitope of paired helical filaments," Neurosci. Lett., 148: 202-206, 1992.
Jackson et al., "Cannabinoids and neuroprotection in CNS inflammatory disease," J. Neurol. Sci., 233: 21-25, 2005.
Li et al., "Melatonin protects SH-SY5Y neuroblastoma cells from calyculin A-induced neurofilament impairment and neurotoxicity," J. Pineal Res., 36: 186-191, 2004.
Lovestone et al., "Alzheimer's disease-like phosphorylation of the microtubule-associated protein tau by glycogen synthase kinase-3 in transfected mammalian cells," Curr. Biol., 4: 1077-1086, 1994.
Mansouri et al., "An alcoholic binge causes massive degradation of hepatic mitochondrial DNA in mice," Gastroenterology, 117(1): 181-190, 1999.
Marchalant et al., "Cannabinoids attenuate the effects of aging upon neuroinflammation and neurogenesis," Neurobiol. Dis., 34: 300-307, 2009.
Martin et al., "Melatonin-induced increased activity of the respiratory chain complexes I and IV can prevent mitochondrial damage induced by ruthenium red in vivo," J. Pinea. Res., 28: 242-248, 2000.
Martin-Moreno et al., "Cannabidiol and other cannabinoids reduce microglial activation in vitro and in vivo: Relevance to Alzheimer's disease," Mol. Pharmacol., 79: 964-973, 2011.
Matsubara, "Melatonin increases survival and inhibits oxidative and amyloid pathology in a transgenic model of Alzheimer's disease," J. Neurochem., 85(5): 1101-1108, 2003.
Maurizi et al., "The mystery of Alzheimer's disease and its prevention by melatonin," Med. Hypotheses, 45(4): 339-340, 1995.
McGilveray, "Pharmacokinetics of cannabinoids," Pain Res. Manag., Autumn, 10 Suppl A:15A-22A, 2005.
Mishra et al., "Tetrahydrocurcumin confers protection against amyloid 0-induced toxicity," Neuroreport, 22: 23-27, 2011.
Nakamura et al., "Reversible effects of acute and long-term administration of delta-9-tetrahydrocannabinol (THC) on memory in the rat," Drug Alcohol Depend., 28(2): 167-175, 1991.
Ng et al., "Melatonin reduces hippocampal beta-amyloid generation in rats exposed to chronic intermittent hypoxia," Brain Res., 1354: 163-171, 2010.
Nunez et al., "Cannabinoid CB2 receptors are expressed by perivascular microglial cells in the human brain: An immunohistochemical study," Synapse, 53: 208-213, 2004.
Octave, "The amyloid peptide and its precursor in Alzheimer's disease," Rev. Neurosci., 6: 287-316, 1995.
Olcese et al., "Protection against cognitive deficits and markers of neurodegeneration by long-term oral administration of melatonin in a transgenic model of Alzheimer disease," J. Pineal Res.,47(1):82-96, 2009.
Olivieri et al., "Melatonin protects SHSY5Y neuroblastoma cells from cobalt-induced oxidative stress, neurotoxicity and increased beta-amyloid secretion," J. Pineal Res., 31(4): 320-325, 2001.
O'Neal-Moffitt, "Prophylactic melatonin significantly reduces Alzheimer's neuropathology and associated cognitive deficits independent of antioxidant pathways in AβPPswe/PSI mice," Mol. Neurodegener., 10: 27, 21 pages, 2015.
Ozaita et al., "Regulation of PI3K/Akt/GSK-3 pathway by cannabinoids in the brain," J. Neurochem., 102(4): 1105-1114, 2007.
Pappolla, "Inhibition of Alzheimer's beta fibrillogenesis by melatonin," Jour. Of Biological Chemistry, 7185-7188, 1998.
Phiel et al., "GSK-3alpha regulates production of Alzheimer's disease amyloid-beta peptides," Nature., 423: 435-439, 2003.
Pillay et al., "Molecular mechanisms, emerging etiological insights and models to test potential therapeutic interventions in Alzheimer's disease," Curr. Alzheimer Res., 1: 295-306, 2004.
Piomelli, "The molecular logic of endocannabinoid signalling," Nat. Rev. Neurosci., 4: 873-884, 2003.
Poeggeler, "Melatonin Reverses the Profibrillogenic Activity of Apoliproprotein E4 on the Alzheimer Amyloid Aβ Peptide," Biochemistry, 40(49): 14995-15001, 2001.

(56) References Cited

OTHER PUBLICATIONS

Priller et al., "Synapse formation and function is modulated by the amyloid precursor protein," The Journal of Neuroscience, 26(27): 7212-7221, 2006.
Proctor & Gray, "GSK3 and p53—is there a link in Alzheimer's disease?" Mol. Neurodegener., 5:7, 15 pages, 2010.
Ramirez et al., "Prevention of Alzheimer's disease pathology by cannabinoids: Neuroprotection mediated by blockade of microglial activation," J. Neurosci., 25: 1904-1913, 2005.
Randall et al., "The functional neurophysiology of the amyloid precursor protein (APP) processing pathway," Neuropharmacology, 59(4-5): 243-267, 2010.
Reitz et al., "Epidemiology of Alzheimer disease," Nat. Rev. Neurol., 7: 137-152, 2011.
Rich et al., "Nonsteroidal anti-inflammatory drugs in Alzheimer's disease," Neurology, 45: 51-55, 1995.
Riedel & Davies, "Cannabinoid function in learning, memory and plasticity," Handb Exp. Pharmacol., 445-477, 2005.
Roch et al., "Increase of synaptic density and memory retention by a peptide representing the trophic domain of the amyloid beta/A4 protein precursor," Proc. Natl. Acad. Sci., 91(16): 7450-7454, 1994.
Rudnitskaya, "Melatonin Attenuates Memory Impairment, Amyloid-β Accumulation, and Neurodegeneration in a Rat Model of Sporadic Alzheimer's Disease," J. Alzheimers Dis., 47(1): 103-116, 2015.
Saxena, "Bioenergetics breakdown in Alzheimer's disease: Targets for new therapies," Int. J. Physiol. Pathophysiol. Pharmacol., 3: 133-139, 2011.
ScienceDaily.com [online], Monmouth Medical Center, "Synthetic Marijuana reduces agitation in patients with Alzheimer's," Nov. 18, 2003, retrieved on Aug. 15, 2019, retrieved from URL<https://www.sciencedaily.com/releases/2003/11/031118073814.htm>.
Singer et al., "A multicenter, placebo-controlled trial of melatonin for sleep disturbance in Alzheimer's disease," Sleep, 36(7): 893-901, 2003.
Song et al., "Melatonin alters the metabolism of the beta-amyloid precursor protein in the neuroendocrine cell line PC12," J. Molecular Neuroscience, 75-92, 1997.
Sun et al., "Lithium inhibits amyloid secretion in COS7 cells transfected with amyloid precursor protein C100," Neurosci. Lett., 321: 61-64, 2002.
Van Sickle et al., "Identification and functional characterization of brainstem cannabinoid CB2 receptors," Science., 310: 329-332, 2005.
Volicer et al., "Effects of dronabinol on anorexia and disturbed behavior in patients with Alzheimer's disease," Int. J. Geriatr. Psychiatry, 12: 913-919, 1997.
Walther et al., "Delta-9-tetrahydrocannabinol for nighttime agitation in severe dementia," Psychopharmacology (Berl.), 185: 524-528, 2006.
Wang et al., "Melatonin ameliorated okadaic-acid induced Alzheimer-like lesions," Acta Pharmacol. Sin., 25: 276-280, 2004.
Wang et al., "Melatonin attenuates isoproterenol-induced protein kinase A over activation and tau hyperphosphorylation in rat brain," J. Pineal Res., 37: 11-16, 2004.
Wang, "Effect of melatonin and melatonylvalpromide on beta-amyloid and neurofilaments in N2a cells," Neurochem. Res.,33(6): 1138-1144, 2008.

* cited by examiner

COMPOUNDS FOR THE TREATMENT OF NEURODEGENERATIVE DISEASES

CROSS-REFERENCE TO RELATED APPLICATIONS

This application claims priority to U.S. Provisional Patent Application No. 62/614,204, filed Jan. 5, 2018, which is incorporated herein by reference in its entirety.

FIELD

This disclosure relates to compounds, as well as methods and compositions comprising the same, for the treatment of neurodegenerative diseases.

INTRODUCTION

Neurodegeneration is the progressive loss of structure or function of neurons, including death of neurons. Many neurodegenerative diseases occur as a result of neurodegenerative processes. Such diseases are currently incurable, resulting in progressive degeneration, cognitive impairment, and/or death of neuron cells. An emerging number of neurodegenerative diseases continue to impact human health. The exact number of neurodegenerative diseases remains elusive, yet estimates project 600 brain disorders impacting 50 million Americans and costing in excess of $5 billion according to the National Institutes of Health. There is a need for new and effective therapies to treat neurodegenerative diseases.

SUMMARY

In an aspect, the disclosure relates to a compound selected from the following:

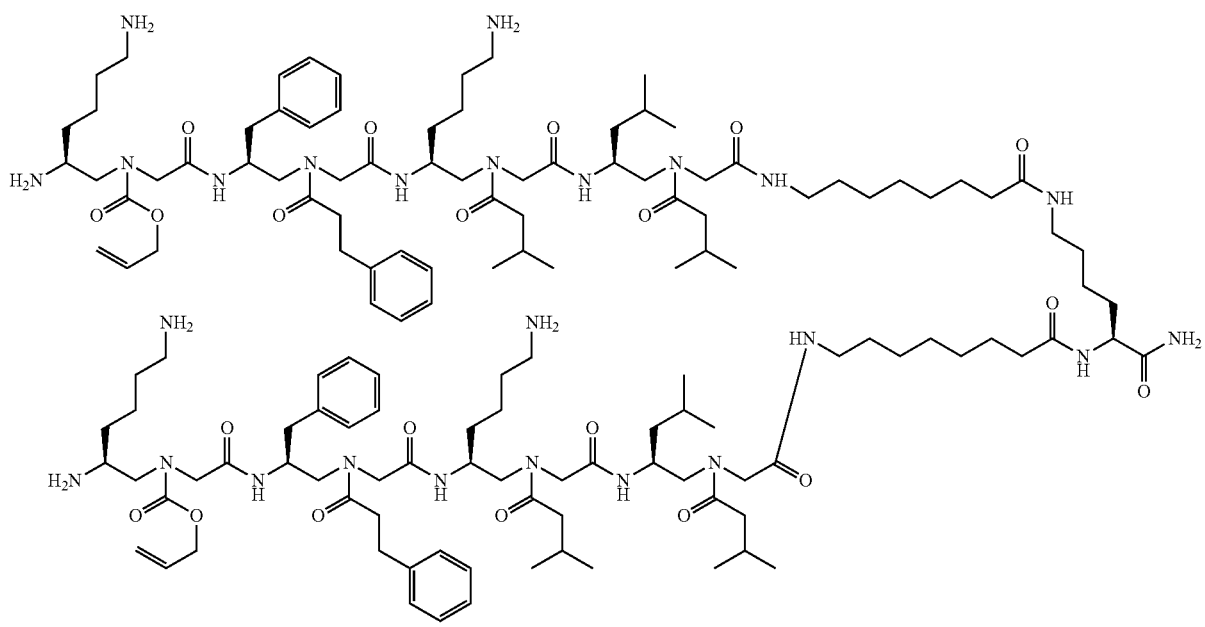

or a pharmaceutically acceptable salt thereof.

In a further aspect, the disclosure relates to a pharmaceutical composition comprising a compound or pharmaceutically acceptable salt thereof as detailed herein, and a carrier.

Another aspect of the disclosure provides a method of treating a neurodegenerative disease in a subject. The method may include administering to the subject a compound or pharmaceutically acceptable salt thereof as detailed herein or a composition comprising the same.

In some embodiments, the neurodegenerative disease is selected from Alzheimer's Disease (AD), amyotrophic lateral sclerosis (ALS), Parkinson's Disease (PD), Huntington's Disease, prion disease, motor neuron disease, spinocerebellar ataxia, spinal muscular atrophy, neuronal loss, cognitive defect, primary age-related tauopathy (PART)/Neurofibrillary tangle-predominant senile dementia, chronic traumatic encephalopathy including dementia pugilistica, dementia with Lewy bodies, neuroaxonal dystrophies, and multiple system atrophy, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis. In some embodiments, the neurodegenerative disease is selected from Alzheimer's Disease (AD) and Huntington's Disease.

Another aspect of the disclosure provides a method of reducing or eliminating an aggregated protein in a subject. The method may include administering to the subject a compound or pharmaceutically acceptable salt thereof as detailed herein or a composition comprising the same, wherein the aggregated protein comprises at least one of tau, synuclein, amyloid-beta, or a combination thereof. In some embodiments, the synuclein comprises alpha-synuclein.

Another aspect of the disclosure provides a method of reducing or inhibiting protein aggregation in a subject. The method may include administering to the subject an effective amount of a compound or pharmaceutically acceptable salt thereof as detailed herein or a composition comprising the same, wherein the protein comprises at least one of tau, synuclein, amyloid-beta, or a combination thereof. In some embodiments, the synuclein comprises alpha-synuclein.

The disclosure provides for other aspects and embodiments that will be apparent in light of the following detailed description and accompanying figures.

BRIEF DESCRIPTION OF THE DRAWINGS

FIG. 6A is a Western blot of Aβ42 alone, Aβ42 with HW-155-1, or Aβ42 with HW-C-9. FIG. 6B (left) is an image of Aβ42 in mouse brain tissue with or without incubation with HW-C-9. FIG. 6B (right) is a graph of the quantification of the density and strength of Aβ42 staining in FIG. 6B (left).

DETAILED DESCRIPTION

Figure 1:
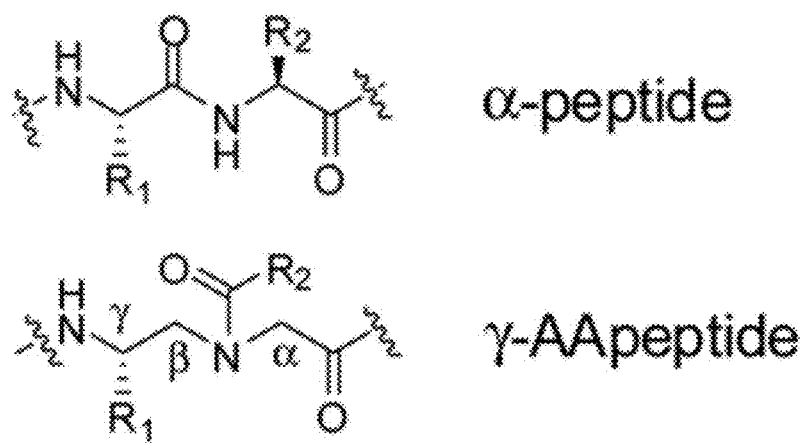
FIG. 1 is the structure of an α-peptide and a γ-AApeptide.

Described herein are compounds that inhibit or disrupt the aggregation of peptides. The compounds may inhibit or reduce the aggregation of peptides such as, for example, aggregates of tau, synuclein, and/or amyloid-beta. Accordingly, the compounds as detailed herein may be used to treat neurodegenerative diseases.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

The term "about" as used herein as applied to one or more values of interest, refers to a value that is similar to a stated reference value. The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 7$^{th}$ Edition, John Wiley & Sons, Inc., New York, 2013; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" or "alkoxyl" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_1$-$C_6$ alkyl" means a straight or branched chain hydrocarbon containing from 1 to 6 carbon atoms. The term "$C_1$-$C_4$ alkyl" means a straight or branched chain hydrocarbon containing from 1 to 4 carbon atoms. The term "$C_1$-$C_3$ alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "alkylamino," as used herein, means at least one alkyl group, as defined herein, is appended to the parent molecular moiety through an amino group, as defined herein.

The term "alkylene" as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino" as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl" as used herein, refers to an aromatic group such as a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl, and tetrahydroquinolinyl.

The term "carboxyl" as used herein, means a carboxylic acid, or —COOH.

The term "cycloalkyl" means a monovalent saturated hydrocarbon ring or a bicyclic group. Cycloalkyl groups have zero heteroatoms and zero double bonds. Cycloalkyl groups are monocyclic, or are fused, spiro, or bridged bicyclic ring systems. Monocyclic cycloalkyl groups contain 3 to 10 carbon atoms, preferably 4 to 7 carbon atoms, and more preferably 5 to 6 carbon atoms in the ring. Bicyclic cycloalkyl groups contain 8 to 12 carbon atoms, preferably 9 to 10 carbon atoms in the ring. Cycloalkyl groups may be substituted or unsubstituted. Cycloalkyl groups include, for example, cyclopropyl, cyclobutyl, cyclopentyl, cyclohexyl, and cycloheptyl.

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, and cycloheptenyl.

The term "cycloalkynyl," as used herein, means a monocyclic or multicyclic ring system containing at least one carbon-carbon triple bond and preferably having from 5-10 carbon atoms per ring or more than 10 carbon atoms per ring.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" or "halo" as used herein, means Cl, Br, I, or F.

The term "heteroalkyl" as used herein, means an alkyl group, as defined herein, in which at least one of the carbons of the alkyl group is replaced with a heteroatom, such as oxygen, nitrogen, and sulfur. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system containing at least one heteroatom independently selected from the group consisting of N, O, and S. The aromatic monocyclic rings are five or six membered rings containing at least one heteroatom independently selected from the group consisting of N, O, and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic" or "heterocyclyl" as used herein means a monocyclic heterocycle, a bicyclic heterocycle (heterobicyclic), or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo [2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3.7}$] decane), and oxa-adamantane (2-oxatricyclo[3.3.1.1$^{3.7}$] decane). The monocyclic, bicyclic, and tricyclic heterocycles are connected to the parent molecular moiety through any carbon atom or any nitrogen atom contained within the rings, and can be unsubstituted or substituted.

The term "heteroarylalkyl" as used herein, refers to a heteroaryl group, as defined herein, appended to the parent molecular moiety through an alkylene group, as defined herein.

The term "heterocyclylalkyl" as used herein, refers to a heterocycle group, as defined herein, appended to the parent molecular moiety through an alkylene group, as defined herein.

The term "hydroxyl" or "hydroxy" as used herein, means an —OH group.

The term "hydroxyalkyl" as used herein, means at least one —OH group, is appended to the parent molecular moiety through an alkylene group, as defined herein.

The term "nitro" means a —NO$_2$ group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$ alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "antagonist" or "inhibitor" refers to a molecule which blocks (e.g., reduces or prevents) a biological activity. An antagonist or inhibitor inhibits the effect of an agonist. An antagonist may be a compound that inhibits or reduces an activity of a polypeptide. An antagonist may indirectly or directly bind a polypeptide and inhibit the activity of the polypeptide, including binding activity or catalytic activity. For example, an antagonist may prevent expression of a polypeptide, or inhibit the ability of a polypeptide to mediate the binding of the polypeptide to a ligand. An "allosteric antagonist" refers to a compound that binds to a polypeptide at a secondary site, distinct from the primary ligand binding site, and inhibits or reduces an activity of the polypeptide. The terms "inhibit" or "inhibiting" mean that an activity is decreased or prevented in the presence of an inhibitor as opposed to in the absence of the inhibitor. The term "inhibition" refers to the reduction or down regulation of a process or the elimination of a stimulus for a process, which results in the absence or minimization of the expression or activity of a biomolecule or polypeptide. Inhibition may be direct or indirect. Inhibition may be specific, that is, the inhibitor inhibits a biomolecule or polypeptide and not others.

As used herein, the term "agonist" refers to a biologically active ligand that binds to its complementary biologically active receptor and activates the receptor either to cause a biological response in the receptor or to enhance a biological activity of the receptor. An agonist may be a molecule or compound that triggers (e.g., initiates or promotes), partially or fully enhances, stimulates, or activates one or more biological activities. An agonist may mimic the action of a naturally occurring substance. Whereas an agonist causes an action, an antagonist blocks the action of the agonist.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject or cell without a compound as detailed herein. A control may be a subject, or a sample therefrom, whose disease state is known. The subject, or sample therefrom, may be healthy, diseased, diseased prior to treatment, diseased during treatment, or diseased after treatment, or a combination thereof. The term "normal subject" as used herein means a healthy subject, i.e., a subject having no clinical signs or symptoms of disease. The normal subject may be clinically evaluated for otherwise undetected signs or symptoms of disease, which evaluation may include routine physical examination and/or laboratory testing. In some embodiments, the control is a healthy control. In some embodiments, the control comprises neurodegenerative disease.

"Neurodegenerative Diseases" are disorders characterized by, resulting from, or resulting in the progressive loss of structure or function of neurons, including death of neurons. Neurodegeneration can be found in many different levels of neuronal circuitry ranging from molecular to systemic. Some neurodegenerative diseases are caused by genetic mutations. Some neurodegenerative diseases are classified as proteopathies because they are associated with the aggregation of misfolded proteins. Neurodegenerative diseases include, for example, Alzheimer's Disease (AD), amyotrophic lateral sclerosis (ALS), Parkinson's Disease (PD), Huntington's Disease, prion disease, motor neuron disease, spinocerebellar ataxia, spinal muscular atrophy, neuronal loss, cognitive defect, primary age-related tauopathy (PART)/Neurofibrillary tangle-predominant senile dementia, chronic traumatic encephalopathy including dementia pugilistica, dementia with Lewy bodies, neuroaxonal dystrophies, and multiple system atrophy, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide such as beta-sheet and alpha-helix. These can form structures commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

A "pharmaceutically acceptable excipient," "pharmaceutically acceptable diluent," "pharmaceutically acceptable carrier," or "pharmaceutically acceptable adjuvant" as used interchangeably herein means an excipient, diluent, carrier, and/or adjuvant that is useful in preparing a pharmaceutical composition that is generally safe, non-toxic, and neither biologically nor otherwise undesirable, and includes an excipient, diluent, carrier, and adjuvant that is acceptable for veterinary use and/or human pharmaceutical use, such as those promulgated by the United States Food and Drug Administration.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a target or activity is to be detected or determined or any sample comprising a compound or composition as detailed herein.

Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. Samples may be obtained before diagnosis, before treatment, during treatment, after treatment, or after diagnosis, or a combination thereof.

"Subject" as used herein can mean a mammal that wants or is in need of the herein described compounds. The subject may be a patient. The subject may be a human or a non-human animal. The subject may be a vertebrate. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. The subject may be of any age or stage of development, such as, for example, an adult, an adolescent, a child, or an infant. In some embodiments, the subject is human. In some embodiments, the subject has a specific genetic marker. In some embodiments, the subject may be diagnosed with or at risk of developing a neurodegenerative disease. The subject or patient may be undergoing other forms of treatment.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides.

"Target" as used herein can refer to an entity that a drug molecule binds. A target may include, for example, a small molecule, a protein, a polypeptide, a polynucleotide, a carbohydrate, or a combination thereof.

A "therapeutically effective amount" is an amount sufficient to elicit a therapeutic effect. Amounts effective for this use will depend on, e.g., the particular composition of the regimen administered, the manner of administration, the stage and severity of the disease, the general state of health of the subject, and the judgment of the prescribing physician. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically effective amount may be administered in one or more administrations (e.g., the composition may be given as a preventative treatment or therapeutically at any stage of disease progression, before or after symptoms, and the like), applications or dosages and is not intended to be limited to a particular formulation, combination or administration route. It is within the scope of the present disclosure that the disclosed compositions may be administered at various times during the course of treatment of the subject. The times of administration and dosages used will depend on several factors, such as the goal of treatment (e.g., treating v. preventing), condition of the subject, etc. and can be readily determined by one skilled in the art. Administration may be adjusted according to individual need and professional judgment of a person administrating or supervising the administration of the compounds used in the present invention.

"Toxic" refers to a substance causing any adverse effect when administered to a subject. The term "non-toxic" refers to a substance that has a relatively low degree to which it can damage a subject. Toxicity can refer to the effect on a whole organism, such as an animal, bacterium, plant, or other subject as defined herein, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom there is a dose below which there is no detectable toxic effect. A composition or compound that is relatively non-toxic may allow a wider range of subjects to be able to safely handle the composition or compound, without serious safety concerns or risks.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment. "Treat," "treatment," or "treating," when referring to protection of a subject from a disease or infection means suppressing, repressing, ameliorating, or completely eliminating the disease or infection. Preventing the disease or infection involves administering a compound or composition of the present invention to a subject prior to onset of the disease or infection. Suppressing the disease or infection involves administering a compound or composition of the present invention to a subject after induction of the disease or infection but before its clinical appearance. Repressing or ameliorating the disease or infection involves administering a compound or composition of the present invention to a subject after clinical appearance of the disease or infection.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequence substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function.

acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. COMPOUNDS

Provided herein is a compound, such as the following:

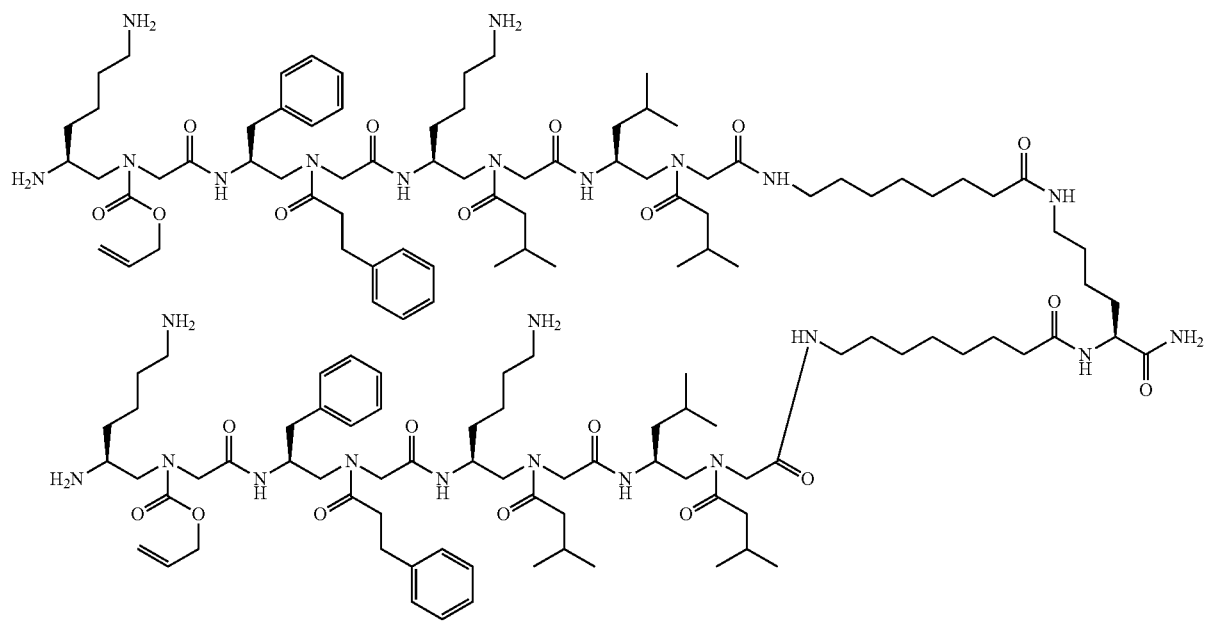

HW-C-9

In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino or a pharmaceutically acceptable salt thereof. The compound shown above may be referred to as "HW-C-9."

The compound may be described as a γ-AApeptide. γ-AApeptides are a class of non-natural peptides. Non-natural peptides may also be referred to as peptidomimetics and may further include peptoids, β-peptides, and N-acylated polyamine. Natural peptides include α-peptides. γ-AApeptides include N-acylated-N-aminoethyl amino acid units derived from γ-PNAs (FIG. 1). Each unit (building block) of a γ-AApeptide is comparable to a dipeptide residue in a natural peptide. As such, γ-AApeptides may project an identical number of functional groups as natural peptides of the same length. Half of the side chains of γ-AApeptides may be chiral. γ-AApeptides may be resistant to proteolytic degradation.

The compound, or a pharmaceutically acceptable salt thereof, may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in *Pure Appl. Chem.*, 1976, 45, 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to the compound shown above, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in the compound are $^{11}$C, $^{13}$N, $^{15}$O, and $^{18}$F. Isotopically-labeled compounds can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. Synthesis of Compounds

Figure 2:
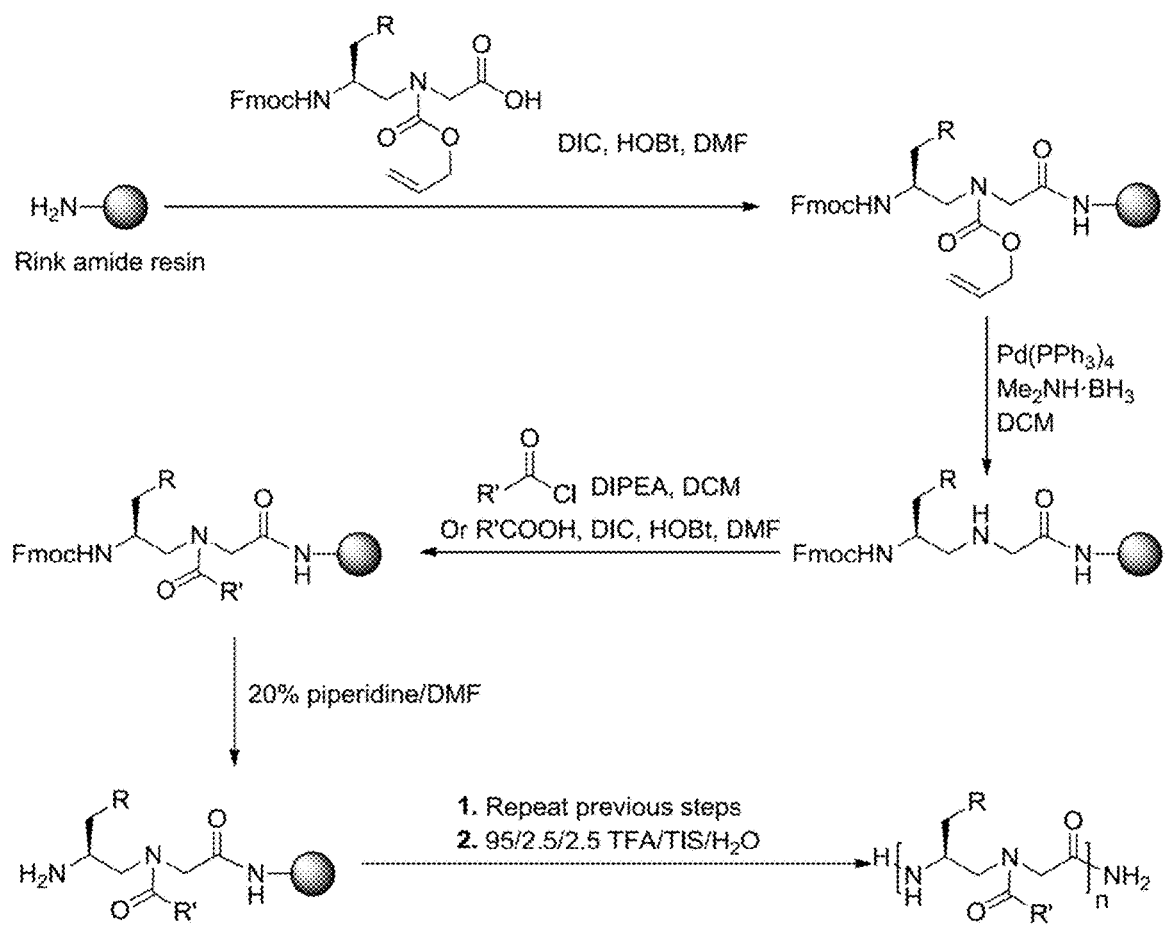
FIG. 2 is a schematic diagram of the synthesis of γ-AApeptides.

The compounds may be made on a solid phase using the protocol published previously (Wu, Haifan et al. γ-AApeptide-based small-molecule ligands that inhibit Aβ aggregation. *Chem. Commun.* 2014, 50, 5206-5208, incorporated herein by reference) and as detailed in Example 1 and FIG. 2. Alternatively, the compounds as detailed herein may be synthetically made by methods known to one of skill in the art. The compounds may be purified by methods known to one of skill in the art, such as, for example, chromatography such as HPLC. The structure and sequence of the compounds may be confirmed by methods known to one of skill in the art, such as, for example, mass spectrometry.

c. Pharmaceutical Compositions

The compounds or salts thereof as detailed herein may be formulated into pharmaceutical compositions accordance with standard techniques well known to those skilled in the pharmaceutical art.

The composition may comprise the compound or salt thereof and a pharmaceutically acceptable carrier. The term "pharmaceutically acceptable carrier," as used herein, means a non-toxic, inert solid, semi-solid or liquid filler, diluent, encapsulating material or formulation auxiliary of any type.

The route by which the disclosed compounds or salts thereof are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). Parenteral administration may include subcutaneous, intravenous, intramuscular, intrathecal, or intrasternal injection, or infusion techniques. Injectable preparations, for example, sterile injectable aqueous or oleaginous suspensions, may be formulated according to the known art using suitable pharmaceutically acceptable carriers. The sterile injectable preparation may also be a sterile injectable solution or suspension in a nontoxic pharmaceutically acceptable carrier. Among the acceptable carriers that may be employed are water, Ringer's solution, isotonic sodium chloride solution. In addition, sterile, fixed oils may be used as a carrier. For this purpose, any bland fixed oil may be employed, including synthetic mono- or diglycerides. In addition, fatty acids such as oleic acid may be used. Other suitable pharmaceutically acceptable carriers may include dimethyl acetamide, surfactants including ionic and non-ionic detergents, and polyethylene glycols. The disclosed compositions may be sterile and stable under the conditions of manufacture and storage. For this purpose, suitable preservatives may be used in the disclosed compositions. For example, the disclosed compositions may comprise benzalkonium chloride, methyl paraben and/or sodium benzoate. The amount of preservative(s) in a composition is typically about 0.01 to about 5%. Suitable pH adjusting additives may also be added to the pharmaceutical composition. Suitable pH adjusting additives may include HCl or NaOH in amounts sufficient to adjust the pH of the pharmaceutical composition. Mixtures of pharmaceutically acceptable carriers such as those disclosed herein may also be used. In some embodiments, the pharmaceutical composition is for administration to a subject's central nervous system. Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 0.1 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, Pa.) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate. In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include a compound or salt thereof, and a carrier including one or more diluents disclosed above in a capsule comprising gelatin. Granules typically comprise a compound or salt thereof, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a compound or salt thereof and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compound into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of a compound and 50% to 99.99% of one or more carriers. Compositions for parenteral administration may typically include 0.1% to 10% of a compound and 90% to 99.9% of one or more carriers. Oral dosage forms may include, for example, at least about 5%, or about 25% to about 50% of a compound. The oral dosage compositions may include about 50% to about 95% of carriers, or from about 50% to about 75% of carriers. The amount of the carrier employed in conjunction with a disclosed compound or salt thereof is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

d. Administration

The compounds or salts thereof as detailed herein, or the pharmaceutical compositions comprising the same, may be administered to a subject. The term "administration" or "administering," as used herein, refers to providing, contacting, and/or delivery of a compound or salt or composition by any appropriate route to achieve the desired effect. Such compositions comprising a compound or salt thereof can be administered in dosages and by techniques well known to those skilled in the medical arts taking into consideration such factors as the age, sex, weight, and condition of the particular subject, and the route of administration.

The compound or salt thereof can be administered prophylactically or therapeutically. In prophylactic administration, the compound or salt thereof can be administered in an amount sufficient to induce a response. In therapeutic applications, the compounds or salts thereof are administered to a subject in need thereof in an amount sufficient to elicit a therapeutic effect. The compound or salt thereof may be administered in a therapeutically effective amount.

The pharmaceutical compositions may include a therapeutically effective amount of the compound or salt thereof. Any suitable therapeutically effective amount of the compound or salt thereof may be used in the pharmaceutical composition. For example, a therapeutically effective amount of a compound or a pharmaceutically acceptable salt thereof, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The compound or salt thereof can be administered by methods well known in the art as described in Donnelly et al. (Ann. Rev. Immunol. 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The compound or salt thereof can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The compound or salt thereof can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the compound is administered intravenously, intranasally, intraarterially, or intraperitoneally to the subject. In some embodiments, the compound or salt thereof is administered intranasally to the subject. In some embodiments, the compound or salt thereof crosses the blood-brain barrier of the subject.

Administration methods are preferably those that are effective to circumvent the blood-brain barrier and are effective to deliver the disclosed compounds or compositions to the central nervous system. For example, delivery methods may include the use of nanoparticles. The particles may be of any suitable structure. Positively charged lipids are particularly preferred for the formulation of such nanoparticles. The preparation of such lipid particles is well known in the art. See, for example, U.S. Pat. No. 4,880,635 to Janoff et al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

The disclosed compounds or salts thereof or compositions may be administered in a bolus directly into the central nervous system. The composition may be administered to the subject in a bolus once, or multiple times. When administered multiple times, the compositions may be administered at regular intervals or at intervals that may vary during the treatment of a subject.

The disclosed compounds or salts thereof or compositions may be administered by continuous infusion into the central nervous system. Non-limiting examples of methods that may be used to deliver the disclosed compounds or salts thereof or compositions into the central nervous system by continuous infusion may include pumps, wafers, gels, foams and fibrin clots. For example, the disclosed compounds or salts thereof or compositions may be delivered into the central nervous system by continuous infusion using an osmotic pump.

The disclosed compounds or salts thereof or compositions may be administered to the patient at any frequency necessary to achieve the desired therapeutic effect. The disclosed compounds or salts thereof or compositions may be administered to the subject as a single dose, or multiple doses over a period of time. For example, the compounds or salts thereof or compositions may be administered once to several times every month, every two weeks, every week, or every day. Administration of the compounds or salts thereof or compositions may be repeated until the desired therapeutic effect has been achieved. For example, the compounds or salts thereof or compositions may be administered once to several times over the course of 1 day, 3 days, 5 days, 1 week, 2 weeks, 3 weeks, 1 month, 2 months, 3 months, 4 months, 5 months, 6 months, 7 months, 8 months, 9 months, 10 months, 11 months, 12 months, or more.

The disclosed compounds or salts thereof or compositions may be administered to a subject in combination with other therapies. For example, the disclosed compounds or salts thereof or compositions may be administered to a subject with other therapies to reduce aggregation of tau, synuclein, amyloid beta, or a combination thereof. As another example, the disclosed compounds or salts thereof or compositions may be administered to a subject in combination with other therapies for the treatment of a neurodegenerative disease.

3. NEURODEGENERATIVE DISEASES

The compounds or salts thereof as detailed herein may be used to treat neurodegenerative diseases. Neurodegenerative diseases include proteinopathies.

Proteinopathies are diseases or disorders in which a protein becomes structurally abnormal. For example, the protein may fail to properly fold into its normal configuration, e.g., become misfolded. In some embodiments, the proteins form aggregates. Aggregates may include fibrillar aggregates, or fibrils. Protein misfolding may include changes to the secondary and/or tertiary structure of a protein. For example, a protein may become structurally abnormal by increasing the beta-sheet secondary structure of the protein. The abnormal structure of the protein may disrupt its function, such as gaining a new function or losing normal function. The structurally abnormal protein may thereby disrupt the function of cells, tissues, and/or organs. Proteinopathies may also be referred to as proteopathies, protein confirmation disorders, or protein misfolding diseases. The compounds or salts thereof as detailed herein may be used to treat proteinopathies associated with protein aggregation and ultimately cell demise. Proteinopathies include, for example, tauopathies, synucleopathies, and disorders characterized by the aggregation of amyloid-beta peptides. Proteinopathies may also include prion disease and amyloidosis. Proteinopathies may be associated with a structurally abnormal protein selected from tau, synuclein, amyloid beta, or a combination thereof. Proteinopathies may be associated with a misfolded or aggregated protein selected from tau, synuclein, amyloid beta, or a combination thereof.

a. Tau

In some embodiments, the compounds or salts thereof as detailed herein inhibit or disrupt the aggregation of tau protein, to treat tauophathies. Tau is a protein that associates with and stabilizes microtubules. Tau may also be referred to as microtubule associated protein tau (MAPT). Tau proteins may also interact with tubulin to stabilize microtubules and promote tubulin assembly into microtubules. There are six isoforms of Tau. Tau proteins are abundant in neurons of the central nervous system and are also expressed at very low levels in central nervous system (CNS) astrocytes and oligodendrocytes.

Tau protein may be phosphorylated by a host of kinases. Phosphorylation of tau is developmentally regulated. Excessive phosphorylation (hyperphosphorylation) or abnormal phosphorylation of tau may result in disruption of microtubule organization, accumulation, and aggregation of tau proteins. In some embodiments tau aggregates do not function properly. For example, tau aggregates may not stabilize microtubules properly.

Tau aggregates include, for example, PHF-tau (paired helical filament), NFTs (neurofibrillary tangles), and gliofibrillary tangles. Tau aggregates may also be described as monomeric, or high molecular weight multimers. Tau aggregates may be insoluble. Tau aggregates may be present in the brain. Tau proteins may be deposited in the form of inclusion bodies within swollen neurons. Aggregation of tau into oligomeric species may lead to various pathologies called tauopathies and may be a major contributor to disease progression.

Tauopathies are a class of neurodegenerative diseases associated with the pathological aggregation of tau protein. Tauopathies include, for example, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis. In some embodiments, the tauopathy comprises Alzheimer's disease (AD).

b. Synuclein

In some embodiments, the compounds or salts thereof as detailed herein inhibit or disrupt the aggregation of synuclein, to treat synucleinopathies. Synucleins are a family of proteins common to vertebrates. Synucleins are primarily expressed in neural tissue and in certain tumors. Synucleins have a highly conserved alpha-helical lipid-binding motif. Synucleins include, for example, alpha-synuclein, beta-synuclein, and gamma-synuclein proteins. Alpha-synuclein may be found in the heart, muscle, brain, and other tissues. In the brain, alpha-synuclein may be found at the tips of neurons at the presynaptic terminal. Alpha-synuclein can interact with phospholipids and proteins. Alpha-synuclein can directly bind to lipid membranes by associating with the negatively charged surfaces of phospholipids. Alpha-synuclein may play a role in maintaining a supply of synaptic vesicles in presynaptic terminals by clustering synaptic vesicles. Alpha-synuclein may help regulate the release of dopamine. Alpha-synuclein may interact with tubulin and have activity as a microtubule-associated protein, similar to tau. In some embodiments, the multiple forms of alpha-synuclein are selected from insoluble, monomeric, and high molecular weight multimers. Expression of gamma-synuclein in breast tumors may be a marker for tumor progression.

Synucleinopathies are neurodegenerative diseases characterized by the abnormal accumulation of aggregates of synucleins such as aggregates of alpha-synuclein in, for example, neurons, nerve fibres, or glial cells. Synucleinopathies include, for example, Parkinson's Disease, dementia with Lewy bodies, neuroaxonal dystrophies, and multiple system atrophy. In some embodiments, synucleinopathies may overlap with tauopathies, potentially because of an interaction between alpha-synuclein and tau.

c. Amyloid-Beta Peptides

In some embodiments, the compounds or salts thereof as detailed herein inhibit or disrupt the aggregation of amyloid-beta peptides, to treat disorders such as Alzheimer's disease. Amyloid-beta peptides (also referred to as "amyloid beta", "A-beta", "Abeta," or "Aβ") are peptides that are found in the brain. The normal function of amyloid-beta peptides may include activation of kinase enzymes, protection against oxidative stress, regulation of cholesterol transport, activity as a transcription factor, and anti-microbial activity (which may be associated with a pro-inflammatory activity of amyloid-beta peptides peptides). Amyloid-beta peptides are formed after sequential cleavage of the amyloid precursor protein (APP), which is a transmembrane glycoprotein. APP can be cleaved by the proteolytic enzymes α-, β- and γ-secretase. Amyloid-beta peptide is generated by successive action of the β- and γ-secretases. The γ-secretase, which produces the C-terminal end of the amyloid-beta peptide, cleaves within the transmembrane region of APP and can generate a number of isoforms of 30 to 51 amino acid residues in length. In some embodiments, amyloid-beta peptide is 36 to 43 amino acids in length. The most common isoforms of the amyloid-beta peptide are 40 amino acids in length (Aβ40) and 42 amino acids in length (Aβ42). The longer form Aβ42 is typically produced by cleavage that occurs in the endoplasmic reticulum, while the shorter form Aβ40 is produced by cleavage in the trans-Golgi network. The Aβ40 form is the more common of the two forms, but Aβ42 may be more fibrillogenic.

Amyloid-beta peptides can aggregate to form flexible soluble oligomers or aggregates, which may exist in several forms. Certain misfolded oligomers (known as "seeds") may induce other amyloid-beta peptides to also take the misfolded oligomeric form, leading to a chain reaction akin to a prion infection. Amyloid-beta aggregates are toxic to nerve cells. Amyloid-beta aggregates may induce tau to misfold. Amyloid-beta peptides are also the main component of amyloid plaques, which are extracellular deposits found in the brains of patients with Alzheimer's disease. Similar plaques appear in some variants of Lewy body dementia and in inclusion body myositis (a muscle disease), while amyloid-beta peptides can also form the aggregates that coat cerebral blood vessels in cerebral amyloid angiopathy. Amyloid plaques are composed of a tangle of regularly ordered fibrillar aggregates called amyloid fibers, which is a protein fold shared by other peptides such as the prions associated with protein misfolding diseases. Soluble oligomeric forms of the amyloid-beta peptide may be causative agents in the development of Alzheimer's disease. Aggregation of amyloid-beta may lead to Alzheimer's disease. In Alzheimer's disease patients, two distinct types of fibrillar protein aggregates are commonly found in brain samples: amyloid plaques comprising deposits of amyloid-beta protein (Aβ) and neurofibrillary tangles consisting of the microtubule-associated protein tau. Genetic and neuropathologic studies suggest that the accumulation of amyloid plaques and/or neurofibrillary tangles may be central to the pathogenesis of Alzheimer's disease.

4. METHODS a. Methods of Treating A Neurodegenerative Disease

Provided herein are methods of treating a neurodegenerative disease in a subject. The method may include administering to the subject an effective amount of a compound or salt or composition as detailed herein. The compounds as detailed herein may disrupt, reduce, inhibit, or prevent the aggregation of molecules such as tau protein, synuclein, and amyloid-beta peptides, or a combination thereof, to treat the neurodegenerative disease. The subject may be diagnosed with or at risk of developing neurodegenerative disease. The subject may be undergoing other forms of treatment for neurodegenerative disease.

In some embodiments, provided is a method for treating Alzheimer's disease in a subject. The method may comprise administering a therapeutically effective amount of the disclosed compounds or salts or compositions to the subject. The subject may be diagnosed with or at risk of developing Alzheimer's disease. The subject may be undergoing other forms of treatment for Alzheimer's disease.

b. Methods of Reducing or Eliminating an Aggregated Protein

Provided herein are methods of reducing or eliminating an aggregated protein in a subject. The method may include administering to the subject an effective amount of a compound or salt or composition as detailed herein. The compounds as detailed herein may disrupt, reduce, inhibit, or prevent the aggregation of molecules including tau protein, synuclein, and amyloid-beta peptides, or a combination thereof. The subject may be diagnosed with or at risk of developing neurodegenerative disease. The subject may be undergoing other forms of treatment for neurodegenerative disease.

Further provided are methods of reducing or inhibiting protein aggregation in a subject. The method may include administering to the subject an effective amount of a compound or salt or composition as detailed herein. The protein may comprise at least one of tau, synuclein, amyloid-beta, or a combination thereof. The subject may be diagnosed with or at risk of developing neurodegenerative disease. The subject may be undergoing other forms of treatment for neurodegenerative disease.

Protein aggregation or fibrillation may be reduced or inhibited relative to a control. In some embodiments, protein aggregation or fibrillation is reduced or inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 98%, or at least about 99% relative to a control. In some embodiments, the control is a healthy subject or sample therefrom, a diseased subject or sample therefrom, a subject or sample therefrom without or prior to treatment, or a subject or sample therefrom at any point earlier in treatment. For example, the disclosed compounds or salts or compositions may reduce or inhibit amyloid-beta fibrillation. In other embodiments, the disclosed compounds or salts or compositions may reduce or inhibit tau protein aggregation. In other embodiments, the disclosed compounds or salts or compositions may reduce or inhibit aggregation of synuclein.

5. EXAMPLES

Example 1

Synthesis of HW-C-9

All Fmoc protected α-amino acids and Rink amide resin (0.7 mmol/g, 200-400 mesh) were purchased from Chem-Impex International, Inc. (Wood Dale, Ill.). TentaGel MB NH2 resin (0.3 mmol/g, 140-170 μm) was purchased from RaPP Polymere GmbH (Tübingen, Germany). All the other solvents and reagents were purchased from either Sigma-Aldrich (St. Louis, Mo.) or Fisher Scientific (Hampton, N.H.). NMR data for building blocks was obtained on a Varian Unitylnova400 spectrometer. High resolution masses of building blocks were determined on an Agilent 6540 Liquid Chromatography/Quadrupole Time-of Flight mass spectrometer. Masses of γ-AApeptides were obtained on an Applied Biosystems 4700 Proteomics Analyzer. MS/MS analysis was carried out with a Thermo LTQ Orbitrap XL. Solid phase synthesis was conducted in peptide synthesis vessels on a Burrell Wrist-Action shaker. γ-AApeptides were analyzed and purified on a Waters Breeze 2 HPLC system, and then lyophilized on a Labcono lyophilizer.

Solid phase synthesis was conducted on Rink amide resin (0.7 mmol/g) in peptide synthesis vessels on a Burrell Wrist-Action shaker (FIG. 2). 100 mg resin (0.07 mmol) was treated with 3 mL 20% Piperidine/DMF solution for 15 min (×2) to remove Fmoc protecting group. The solution was drained and beads were washed with DCM (3×3 mL) and DMF (3×3 mL). A solution of γ-AApeptide building block (2 equiv.) (Niu, et al. *Chemical communications*, Cambridge, England 2011, 47, 12197-12199; Niu, et al. *Org. Biomol. Chem.* 2011, 9, 6604-6609; Niu, et al. *New Journal of Chemistry* 2011, 35, 542-545; Wu, et al. *Chem. Sci.* 2012, 3 2570-2575; Wu, et al. Submitted), HOBt (38 mg, 0.28 mmol), and DIC (44 μL, 0.28 mmol) in 3 mL DMF was shaken for 5 min, and then added to the resin in a peptide synthesis vessel. The mixture was allowed to react at room temperature for 6 h and drained. The beads were washed with DCM (3×3 mL) and DMF (3×3 mL), followed by a capping reaction with 500 μL acetic anhydride in 3 mL Pyridine. After washing with DMF (3×3 mL) and DCM (3×3 mL), to the beads were added Pd(PPh$_3$)$_4$ (8 mg, 0.007 mmol) and Me$_2$NH·BH$_3$ (25 mg, 0.42 mmol) in 3 mL DCM (Gomez-Martinez, et al. *J. Chem. Soc. Perk. T* 1, 1999, 2871-2874). The alloc deprotection reaction was shaken for 10 min and repeated one more time. The beads were washed with DCM and DMF, followed by the reaction with acid chloride (4 equiv.) and DIPEA (6 equiv.) in 3 mL DCM for 30 min (×2) or with carboxylic acid (4 equiv.), HOBt (8 equiv.), and DIC (8 equiv.) for 4 h (×2).

Figure 3:
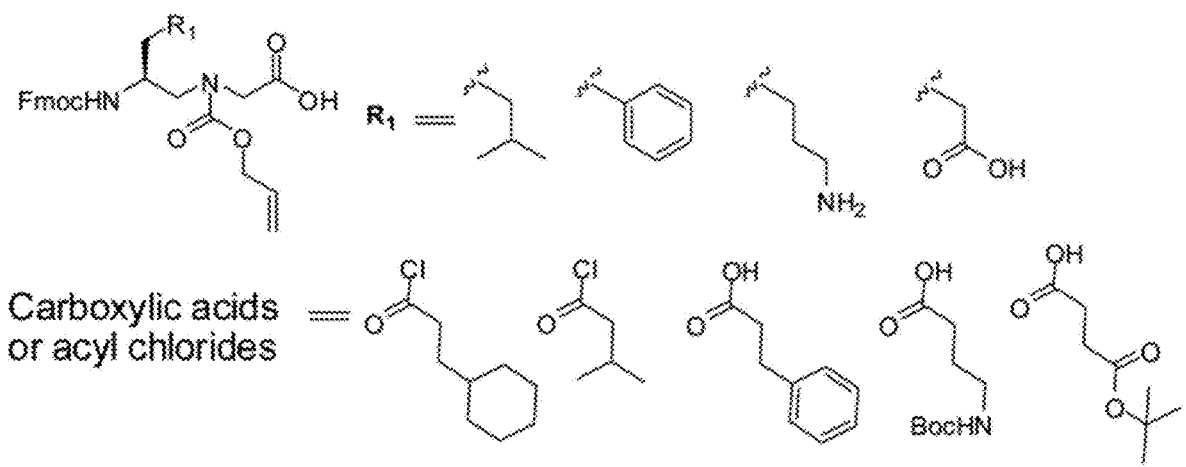
FIG. 3 is a schematic diagram of N-Alloc protected γ-AApeptide building blocks and acylating agents (carboxylic acids and acyl chlorides) that may be used in the preparation of γ-AApeptides.

The previous steps were repeated until the desired sequences were obtained. Examples of N-Alloc protected γ-AApeptide building blocks and acylating agents (carboxylic acids and acyl chlorides) that may be used in the preparation of γ-AApeptides are shown in FIG. 3. After that, the resin were washed with DCM and dried in vacuo. Peptide cleavage was done in a 4 mL vial by treating resin with TFA/H$_2$O/TIS (95/2.5/2.5) for 2 h. The solvent was evaporated and the crude was analyzed and purified on an analytical (1 mL/min) and a preparative (20 mL/min) Waters HPLC systems, respectively. 5% to 100% linear gradient of solvent B (0.1% TFA in acetonitrile) in solvent A (0.1% TFA in water) over 40 min was used. The HPLC traces were detected at 215 nm. The products were confirmed on an Applied Biosystems 4700 Proteomics Analyzer. Then, the desired fractions were collected and lyophilized.

Example 2

Effect of HW-C-9 on Aβ42

The effect of HW-C-9 on Aβ42 was analyzed using the Thioflavin T (ThT) spectroscopic assay. Thioflavin T (ThT) is a benzothiazole salt obtained by the methylation of dehydrothiotoluidine with methanol in the presence of hydrochloric acid. ThT was used as a dye to visualize and quantify the presence or fibrilization of misfolded protein aggregates. Briefly, HW-C-9 in Tris Buffered Saline (TBS, pH 7.5) containing 10 μM ThT was added into a black 96 well plate. Aβ42 protein monomer was freshly thawed and used to make a stock 5 μM solution in TBS. An equal volume of Aβ42 solution was added to each well to a final concentration of 2.5 μM Aβ42 and incubated at 37° C. Time-dependent fluorescence change was monitored by a Synergy 2 plate reader at an excitation wavelength of 440 nm and emission at 482 nm. The fluorescence intensity of ThT was measured over time, as ThT changed fluorescence intensity upon binding to the Aβ42 protein aggregates. 100% aggregation was defined as the fluorescence change of 2.5 μM Aβ42 in TBS buffer containing 5 μM ThT after 24 hours.

Figure 4:
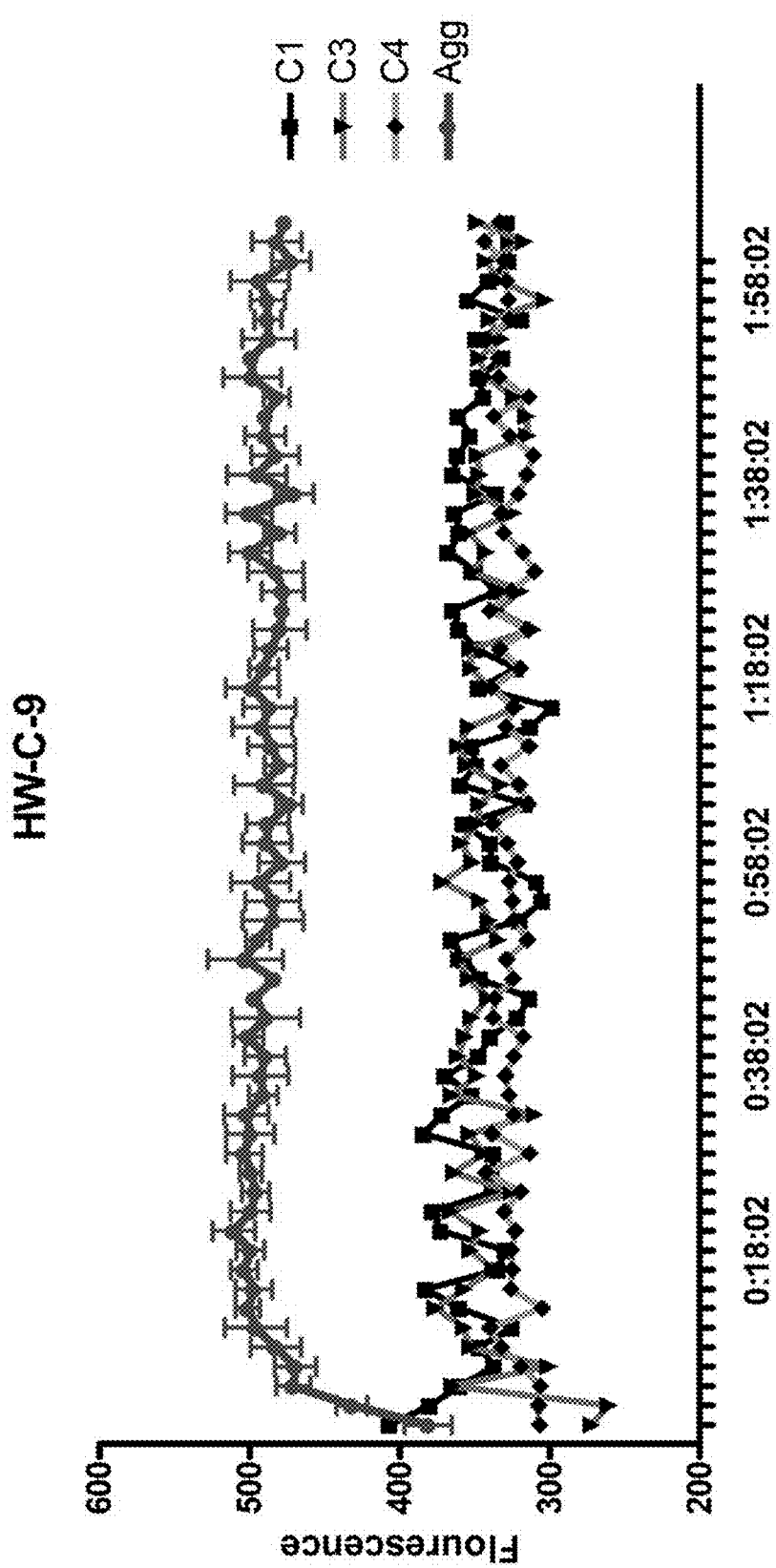
FIG. 4 is a graph of ThT assay results showing the effect of HW-C-9 on amyloid-beta (Aβ) aggregates.

Results are shown in FIG. 4. In FIG. 4, C1 is 1 μM of HW-C-9, C3 is 5 μM of HW-C-9, and C4 is 10 μM of HW-C-9. Aβ42 was present in all samples at a concentration of 5 μM. The top curve (red line, "Agg") is the Aβ42-only control. The results indicated that HW-C-9 can inhibit Aβ42 aggregation at all concentrations tested.

Example 3

Effect of HW-C-9 on Tau Protein

Figure 5:
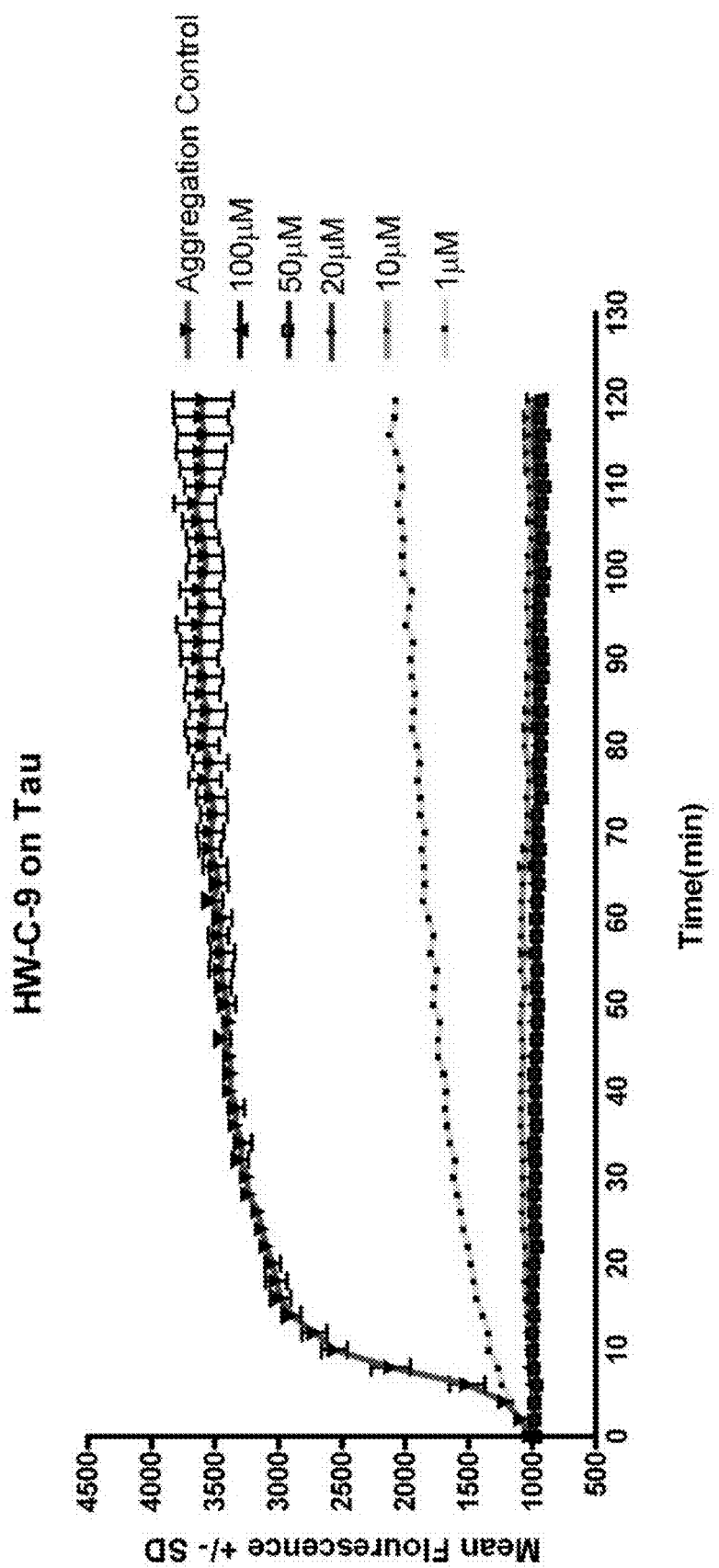
FIG. 5 is a graph of ThT assay results showing the effect of HW-C-9 on Tau protein aggregates.

The effect of HW-C-9 on recombinant human tau protein was analyzed using the ThT assay, as detailed in Example 2, but with tau protein in place of Aβ42. Results are shown in FIG. 5. In FIG. 5, C1 is 100 μM of HW-C-9, C2 is 50 μM of HW-C-9, C3 is 20 μM of HW-C-9, C4 is 10 μM of HW-C-9, and C5 is 1 μM of HW-C-9. Tau was present in all samples at a concentration of 10 μM. The top curve (red line with black triangle, "Aggregation control") is the Tau-only control. The results indicated that HW-C-9 can inhibit aggregation of tau protein at all concentrations tested.

Example 4

Effect of HW-C-9 on Aβ42

The effect of HW-C-9 on Aβ42 was analyzed, with HW-155-1 used as a control. HW-155-1 is a monomer of HW-C-9 and has the structure shown below:

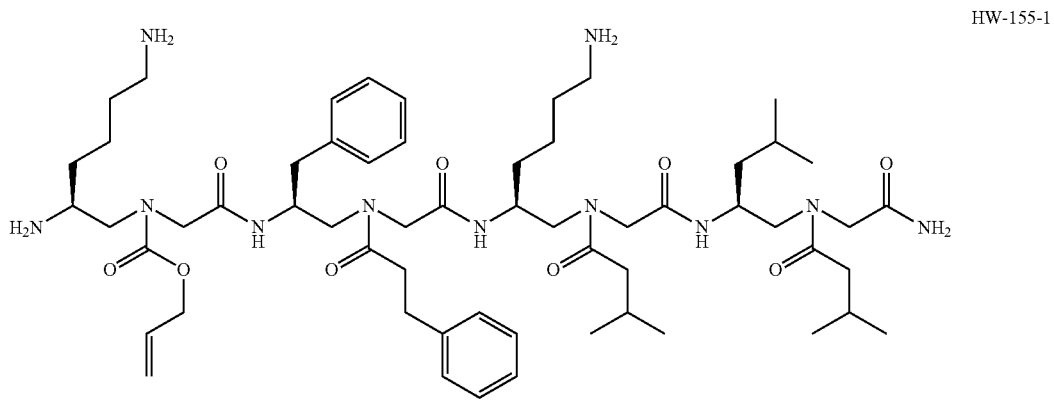 [SMILES: C=CCOC(=O)N(CC(=O)N[C@@H](Cc1ccccc1)CN(CC(=O)N[C@@H](CCCCN)CN(CC(=O)N[C@@H](CC(C)C)CN(CC(N)=O)C(=O)CC(C)C)C(=O)CC(C)C)C(=O)CCc1ccccc1)C[C@@H](N)CCCCN]

HW-155-1

Figure 6A:
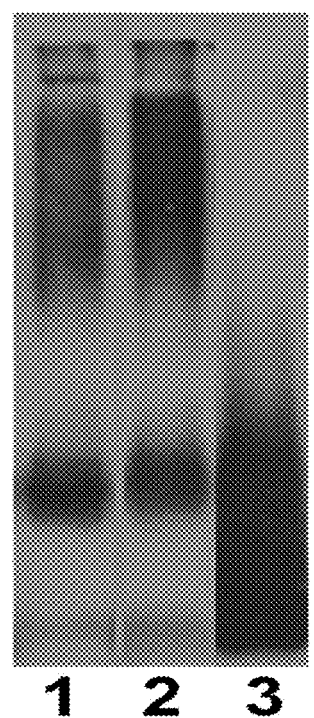
FIG. 6A and FIG. 6B are the results of assays to examine the effect of HW-C-9 on the aggregation of Aβ42.
Figure 6B:
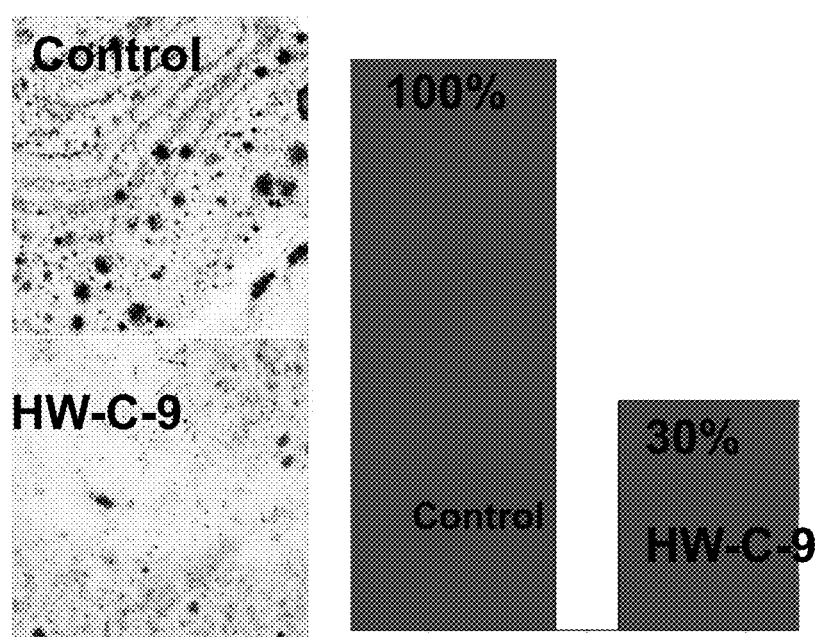

Results from the experiment are shown in FIG. 6A and FIG. 6B. Shown in FIG. 6A is a Western blot of Aβ42, wherein lane 1 is 20 μM of Aβ, lane 2 is 40 μM of HW-155-1 as a control and 20 μM of Aβ, and lane 3 is 40 μM of HW-C-9 and 20 μM of Aβ. Shown in FIG. 6B on the left is mouse brain tissue incubated overnight with and without 25 μM of HW-C-9, and then immunohistochemically stained with Aβ42 antibodies. On the right of FIG. 6B is a graphical quantification of the density and strength of the antibody stains. The results indicated that HW-C-9 can inhibit aggregation of Aβ42 and remove amyloid plaques.

Example 5

Effect of HW-C-9 on Synuclein

Figure 7:
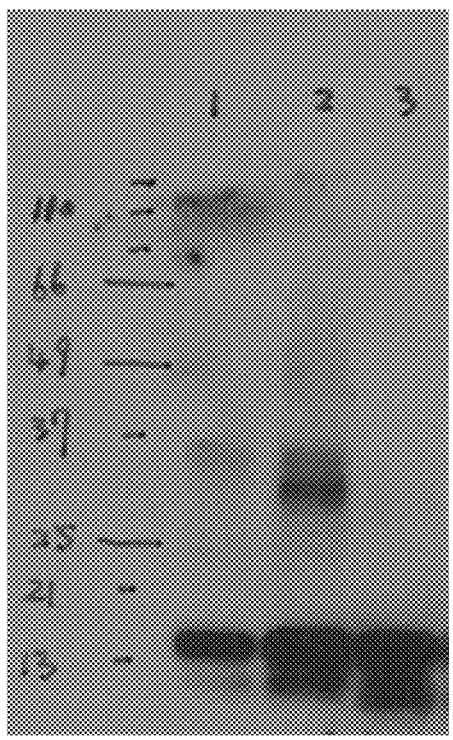
FIG. 7 is a Western blot of human recombinant alpha-synuclein without aggregation, human recombinant alpha-synuclein with aggregation, and human recombinant alpha-synuclein with aggregation but in the presence of HW-C-9.

The effect of HW-C-9 on synuclein was analyzed with a Western blot. Results are shown in FIG. 7, wherein lane 1 is human recombinant alpha-synuclein (stained with goat anti-human alpha-synuclein antibody) without aggregation as a control, lane 2 is human recombinant alpha-synuclein (stained with goat anti-human alpha-synuclein antibody) aggregated for 7 days, and lane 3 is human recombinant alpha-synuclein (stained with goat anti-human alpha-synuclein antibody) aggregated for 7 days in the presence of 25 µg/mL of HW-C-9. The results indicated that HW-C-9 can inhibit aggregation of alpha-synuclein.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A compound selected from the following:

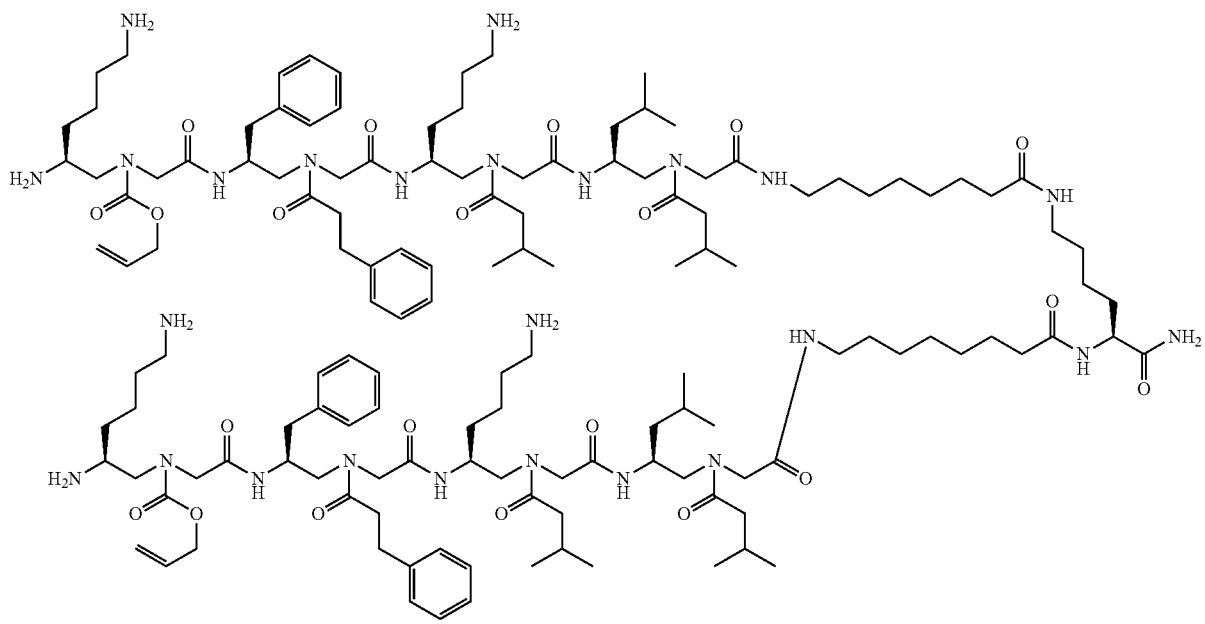

or a pharmaceutically acceptable salt thereof.

Clause 2. A pharmaceutical composition comprising the compound or salt of clause 1, and a carrier.

Clause 3. A method of treating a neurodegenerative disease in a subject, the method comprising administering to the subject the compound or salt of clause 1 or the composition of clause 2.

Clause 4. The method of clause 3, wherein the neurodegenerative disease is selected from Alzheimer's Disease (AD), amyotrophic lateral sclerosis (ALS), Parkinson's Disease (PD), Huntington's Disease, prion disease, motor neuron disease, spinocerebellar ataxia, spinal muscular atrophy, neuronal loss, cognitive defect, primary age-related tauopathy (PART)/Neurofibrillary tangle-predominant senile dementia, chronic traumatic encephalopathy including dementia pugilistica, dementia with Lewy bodies, neuroaxonal dystrophies, and multiple system atrophy, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

Clause 5. The method of clause 4, wherein the neurodegenerative disease is selected from Alzheimer's Disease (AD) and Huntington's Disease.

Clause 6. A method of reducing or eliminating an aggregated protein in a subject, the method comprising administering to the subject the compound or salt of clause 1 or the composition of clause 2, wherein the aggregated protein comprises at least one of tau, synuclein, amyloid-beta, or a combination thereof.

Clause 7. The method of clause 6, wherein the synuclein comprises alpha-synuclein.

Clause 8. A method of reducing or inhibiting protein aggregation in a subject, the method comprising administering to the subject an effective amount of the compound or salt of clause 1 or the composition of clause 2, wherein the protein comprises at least one of tau, synuclein, amyloid-beta, or a combination thereof.

Clause 9. The method of clause 8, wherein the synuclein comprises alpha-synuclein.

The invention claimed is:

1. A compound selected from the following:

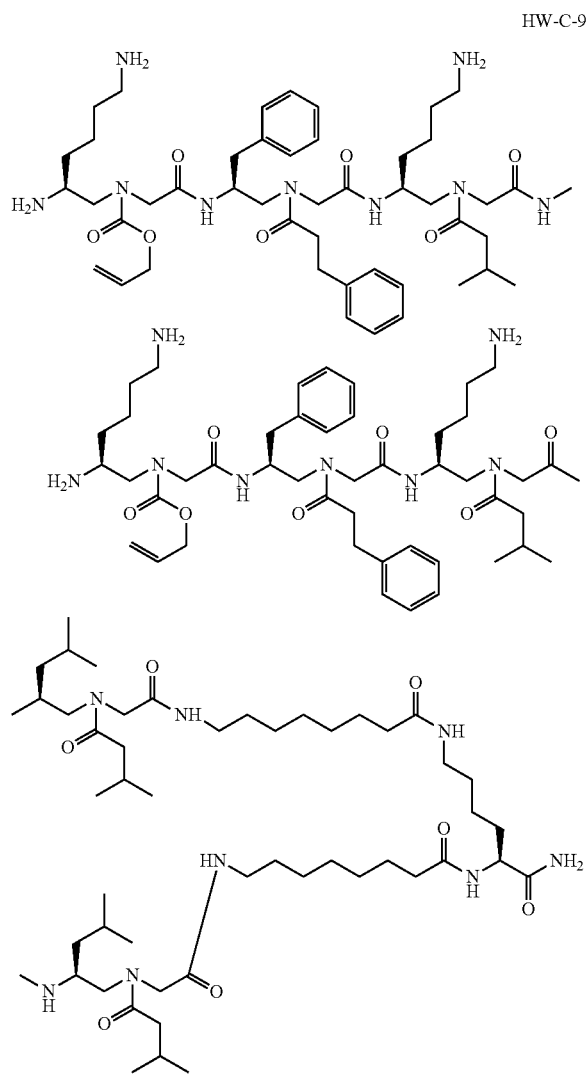

or a pharmaceutically acceptable salt thereof.

2. A pharmaceutical composition comprising the compound or salt of claim 1, and a carrier.

3. A method of treating a neurodegenerative disease in a subject, the method comprising administering to the subject the compound or salt of claim 1, wherein the neurodegenerative disease is selected from Alzheimer's Disease (AD), amyotrophic lateral sclerosis (ALS), Parkinson's Disease (PD), Huntington's Disease, prion disease, motor neuron disease, spinocerebellar ataxia, spinal muscular atrophy, primary age-related tauopathy (PART)/Neurofibrillary tangle-predominant senile dementia, chronic traumatic encephalopathy, dementia pugilistica, dementia with Lewy bodies, neuroaxonal dystrophies, multiple system atrophy, progressive supranuclear palsy, Pick's Disease, corticobasal degeneration, frontotemporal dementia with parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

4. The method of claim 3, wherein the neurodegenerative disease is selected from Alzheimer's Disease (AD), amyotrophic lateral sclerosis (ALS), Parkinson's Disease (PD), and Huntington's Disease.

5. The method of claim 3, wherein the neurodegenerative disease is Alzheimer's Disease (AD).

6. A method of reducing or eliminating an aggregated protein in a subject, the method comprising administering to the subject the compound or salt of claim 1, wherein the aggregated protein comprises at least one of tau, synuclein, amyloid-beta, or a combination thereof.

7. The method of claim 6, wherein the synuclein is alpha-synuclein.

8. A method of reducing or inhibiting protein aggregation in a subject, the method comprising administering to the subject an effective amount of the compound or salt of claim 1, wherein the protein comprises at least one of tau, synuclein, amyloid-beta, or a combination thereof.

9. The method of claim 8, wherein the synuclein is alpha-synuclein.

* * * * *